US007999076B2

(12) United States Patent
Zal et al.

(10) Patent No.: US 7,999,076 B2
(45) Date of Patent: Aug. 16, 2011

(54) USE OF A HIGH MOLECULAR WEIGHT EXTRACELLULAR HEMOGLOBIN FOR THE MANUFACTURE OF A MEDICAMENT FOR TREATING AND/OR PREVENTING DISEASES BY INHIBITION OF CALCIUM

(75) Inventors: Franck Zal, Morlaix-Ploujean (FR); Morgane Rousselot, Saint-Pol-de-Leon (FR)

(73) Assignee: Centre National De La Recherche, Paris (FR)

( * ) Notice: Subject to any disclaimer, the term of this patent is extended or adjusted under 35 U.S.C. 154(b) by 401 days.

(21) Appl. No.: 12/223,185

(22) PCT Filed: Jan. 23, 2007

(86) PCT No.: PCT/EP2007/050651
§ 371 (c)(1),
(2), (4) Date: Aug. 15, 2008

(87) PCT Pub. No.: WO2007/085596
PCT Pub. Date: Aug. 2, 2007

(65) Prior Publication Data
US 2010/0234275 A1    Sep. 16, 2010

Related U.S. Application Data

(60) Provisional application No. 60/761,358, filed on Jan. 24, 2006.

(51) Int. Cl.
*A61K 38/42* (2006.01)
*A61P 9/12* (2006.01)
(52) U.S. Cl. .............................. 530/385; 514/6; 424/9.1

(58) Field of Classification Search ............... 530/385; 514/6; 424/9.1
See application file for complete search history.

(56) References Cited

U.S. PATENT DOCUMENTS
2003/0181358 A1    9/2003   Zal et al.

OTHER PUBLICATIONS

Paul A. Meglitsch, "Invertebrate Zoology", second edition, pp. 364-427, (1972).
Katy Lisias Gondim Dias et al., "Cardiovascular Effects Induced by Reticuline in Normotensive Rats", Planta Med, vol. 70, Jan. 25, 2004, pp. 328-333.
Gordon S. Stokes, MD, FRACP, "Systolic Hypetension in the Elderly: Pushing the Frontiers of Therapy A Suggested New Approach", vol. VI, No. IV, Apr. 2004, pp. 192-197.
Ryan P. Jewell, M.D. et al., "Inhibition of Ca ++ sparks by oxyhemoglobin in rabbit cerebral arteries", J. Neurosurg., vol. 100, Feb. 2004, pp. 295-302.
Roberto Fogari et al., "Effect of Antihypertensive Agents on Quality of Life in the Elderly", Drugs Aging, vol. 21, No. 6, 2004, pp. 377-393.

*Primary Examiner* — Chih-Min Kam
(74) *Attorney, Agent, or Firm* — Birch, Stewart Kolasch & Birch, LLP

(57) ABSTRACT

The present invention relates to the use of a high molecular weight extracellular hemoglobin for the manufacture of a medicament for treating and/or preventing diseases by inhibition of calcium. Advantageously, the extracellular hemoglobin is obtained from Annelids. In particular, the invention concerns the use of a high molecular weight extracellular hemoglobin for the manufacture of a medicament for treating and/or preventing cardiovascular diseases, such as hypertension, angina such as angina pectoris, Raynaud's disease, arteriopathy, tachycardia, vasospasm, ischemia, myocardial infarction, congestive heart failure, arrhythmia or cerebrovacular accident.

9 Claims, 6 Drawing Sheets

Figure 1A:
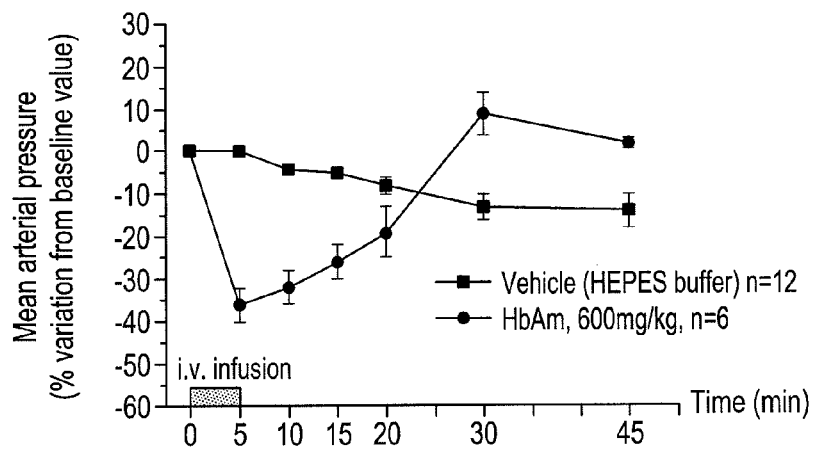

USE OF A HIGH MOLECULAR WEIGHT EXTRACELLULAR HEMOGLOBIN FOR THE MANUFACTURE OF A MEDICAMENT FOR TREATING AND/OR PREVENTING DISEASES BY INHIBITION OF CALCIUM

This application is the National Phase of PCT/EP2007/050651 filed on Jan. 23, 2007, which claims priority under 35 U.S.C. 119(e) to U.S. Provisional Application No. 60/761,358 filed on Jan. 24, 2006 the entire contents of which are hereby incorporated by reference.

The present invention relates to the use of a high molecular weight extracellular hemoglobin for the manufacture of a medicament for treating and/or preventing diseases by inhibition of calcium. Advantageously, the extracellular hemoglobin is obtained from Annelids. In particular, the invention concerns the use of a high molecular weight extracellular hemoglobin for the manufacture of a medicament for treating and/or preventing cardiovascular diseases, such as hypertension, angina such as angina pectoris, Raynaud's disease, arteriopathy, tachycardia, vasospasm, ischemia, myocardial infarction, congestive heart failure, arrhythmia or cerebrovacular accident.

Worldwide, efficient treatments of cardiovascular diseases, such as hypertension, are at stake. In France, more than 14 million people suffer from hypertension. In the U.S.A., about 65 million American adults, nearly one in three, have high blood pressure. Once high blood pressure develops, it usually lasts a lifetime.

High blood pressure or hypertension is called "the silent killer" because it usually has no symptoms. Some people may not find out they have it until they have trouble with their heart, brain, or kidneys. In France, only 73% of the people actually know their condition. However, when high blood pressure is not found and treated, it can cause very serious troubles such as heart failure, heart attack, stroke, kidney failure, infarct, apoplexy, or cerebral ischemic attack.

In many people with high blood pressure, a single specific cause is not known. In some people, high blood pressure is the result of another medical problem or medication. In many cases, many people get high blood pressure as they get older. Over half of all Americans age 60 and older have high blood pressure. Besides, the chances of getting hypertension are also higher when people are overweight, do not eat a healthy diet (for instance people who eat too much salt or drink too much alcohol), do not get exercise, or smoke too much, or else when people have a family history of high blood pressure.

Blood pressure medicines work in different ways to lower blood pressure. Several types of medicines can be used to treat high blood pressure, such as diuretics, beta blockers, alpha blockers, angiotensin converting enzyme inhibitors, angiotensin II receptor blockers, calcium channel blockers, nervous system inhibitors, or vasodilators. In particular, calcium channel blockers keep calcium from entering the muscle cells of the heart and blood vessels. As a result, they relax blood vessels and increase the supply of blood and oxygen to the heart while reducing its workload. The blood pressure usually thus goes down.

But, often, two or more drugs are needed for the treatment of high blood pressure. Besides, common high blood pressure medicines are needed to be taken for a long time. And, even if medicines usually control blood pressure, they often cannot cure it.

Furthermore, usual high blood pressure medicines often cause some unwanted side effects, such as breathing difficulty, coughing, or wheezing, irregular or fast, pounding heartbeat, skin rash, slow heartbeat, swelling of ankles, feet, or lower legs, constipation, diarrhea, flushing and feeling of warmth, headache, unusual tiredness or weakness.

For instance, flunarizine, which is a calcium channel blocking agent, can cause drowsiness and increased appetite and/or weight gain. Bepridil and nifedipine can cause nausea and dizziness or lightheadedness.

Some side effects can be very serious. For instance, the main side effect of dantrolene, when chronically used or when overdosed, is hepatitis.

There was thus a need for a new drug for treating cardiovascular diseases without having the side effects and the drawbacks of the commonly used drugs, such as the ones mentioned above.

The invention makes it possible to remedy these disadvantages and major drawbacks.

The inventors thus discovered that a high molecular weight extracellular hemoglobin, advantageously the extracellular hemoglobin obtained from Annelids, can be efficiently used as a calcium inhibitor, by chelation of calcium, and can be efficiently used for the treatment of cardiac diseases, vascular diseases, or neurological diseases, such as hypertension.

High molecular weight extracellular hemoglobins, in particular the extracellular hemoglobin obtained from Annelids, were already used as blood substitutes (WO 01/92320), but they were never used as calcium chelating agent or for treating cardiac diseases, vascular diseases, or neurological diseases, in particular cardiovascular diseases.

The present invention relates to the use of a high molecular weight extracellular hemoglobin for the manufacture of a medicament for treating and/or preventing diseases by inhibition of calcium.

The extracellular hemoglobin used in the present invention is a giant biopolymer having a high molecular weight of between several hundred thousand Daltons and several million Daltons, advantageously between 0.1 and 10 million Daltons, more advantageously between 1 and 5 million Daltons, and most advantageously between 3 and 4 million Daltons. The hemoglobin is thus approximately 60 times bigger than intracellular hemoglobins of vertebrates.

The giant biopolymers of the present invention are made up of approximately 150 to 200 polypeptide chains belonging to 1 to 15 different types, some of the polypeptide chains are linked by covalent bonds. The polypeptide chains are generally grouped together in two categories. The first category, consisting approximately of 144 to 192 elements, groups together the "functional" polypeptide chains, carrying an active site and capable of reversibly binding oxygen; these are globin-type chains of masses between 15 and 18 kDa, which are very similar to the α- and β-type chains of vertebrates. The second category, consisting approximately of 36 to 42 elements, groups together "structural" polypeptide chains, having masses between 22 and 27 kDa, having few or no active sites but allowing the assembling of the "twelfths" (assembling of trimers and monomers).

Advantageously according to the present invention, the extracellular hemoglobin contains free cystein residues on some of the globin chains.

The term "extracellular hemoglobin" refers to a hemoglobin not contained in the cells and dissolved in the blood.

Some of the globin chains of extracellular hemoglobin are stabilised between themselves, by covalent bonds, in particular intermolecular disulphide bridges, and the globin chains may be auto-stabilised by intramolecular disulphide bridges.

The expression "the globin chains of extracellular haemoglobin are stabilised between themselves, by covalent bonds" refers to the presence of interchain disulphide bonds between two or more globin chains.

The expression "the globin chains are auto-stabilized" refers to the presence of intrachain disulphide bonds on each globin chain.

According to an advantageous embodiment of the present invention, the extracellular hemoglobin is obtained from Annelids. These extracellular hemoglobin molecules are present in the three classes of Annelids: Polychaetes, Oligochaetes and Achaetes and even in the Vestimentifers.

Annelids have been extensively studied for their extracellular hemoglobin. The images obtained of extracellular hemoglobins of *Arenicola* have revealed hexagonal elements. Each hemoglobin molecule is made up of two superimposed hexagons, called a hexagonal bilayer, and each hexagon is itself made up of six elements in the form of a drop of water called a hollow globular structure or "twelfth". The native molecule is formed from twelve of these sub-units, of a molecular mass of approximately 250 kDa. There is particular interest in *Arenicola marina*, a polychaete annelid of the intertidal ecosystem. Moreover, the structure of its extracellular hemoglobin is already known.

According to an advantageous embodiment of the invention, the extracellular hemoglobin comprises structural chains conferring a hexagonal structure on the hemoglobin.

The classification to which reference is made when using the term Annelids is that described in Meglitsch P. A., Invertebrate Zoology, Oxford University Press, Oxford, p. 834, (1972)

Particularly advantageously according to the present invention, the extracellular hemoglobin invention is obtained from Polychaete Annelids, preferably from *Arenicola marina*.

According to another embodiment of the invention, the extracellular hemoglobin can also be obtained by recombinant expression (See protocol in WO 2005/037392).

According to an advantageous embodiment of the invention, the extracellular hemoglobin is naturally polymerised, non-toxic, non-allergenic, and non-immunogenic.

The expression "non-toxic" means that the hemoglobin does not cause any pathological disorder of an immune-reaction, allergic or nephrotoxic type.

Besides, advantageously, the extracellular hemoglobin has no pathogenic agent, and does not lead to physiopathology in animals.

The expression "has no pathogenic agent" refers to the absence of identified microorganisms or viruses.

The absence of pathological disorders indirectly implies the absence of pathogens.

None of the side effects likely to be encountered with products of the prior art, in particular oedemas, problems of immunogenicity and nephrotoxicity do not exist within the framework of the present invention.

According to an advantageous embodiment of the invention, the extracellular hemoglobin is able to chelate to divalent ions, in particular to calcium, thus forming complexing compounds. The extracellular hemoglobin is thus advantageously a calcium chelator, enabling to bind to calcium.

The studies conducted by the inventors of the present invention with respect to properties of the extracellular hemoglobin self-assembly (in particular the Annelid extracellular hemoglobin self-assembly) revealed the importance of the divalent cations $Ca^{2+}$ and $Mg^{2+}$ in the maintenance of the quaternary structure of the hemoglobin at basic pH. The quaternary structure of the extracellular hemoglobin is stabilized at slightly basic pH, in particular at physiologic pH (pH between 7 and 8), by those divalent cations.

The divalent cations $Ca^{2+}$ and $Mg^{2+}$ allow the maintenance of the quaternary structure of the extracellular hemoglobin (in particular the Annelid extracellular hemoglobin). These ions prevent dissociation and slow dissociation kinetics of the extracellular hemoglobin at alkaline pH.

The extracellular hemoglobin, once administered under human physiological conditions, binds the calcium present in blood to maintain its quaternary structure. This instantaneous reaction leads to a reduction in the level of physiological calcium.

It can thus be concluded that the extracellular hemoglobin of the present invention is advantageously an equivalent to calcium inhibitors, by chelating and binding blood calcium. Today, calcium inhibitors refer to the drugs that inhibit the entrance of calcium into the cells by voltage-dependant calcium channels. The extracellular hemoglobin of the present invention advantageously has effects similar to calcium inhibitors, since the extracellular hemoglobin is a calcium chelating agent.

According to an embodiment of the invention, the extracellular hemoglobin advantageously has several effects:

Cardiac Effects: for instance on the level of nodal tissue: slowing the action potential's slow diastolic depolarization in phase 0, or on the level of the myocardium: possibility of a negative inotropic effect Vascular effects: general vasodilatation, of coronary or cerebral predominance Effects on nonvascular smooth fibers: relaxation Neurological effects: reduction in excitability.

The present invention more particularly relates to the use of the high molecular weight extracellular hemoglobin for the manufacture of a medicament for treating and/or preventing cardiac diseases, vascular diseases, or neurological diseases, in particular cardiovascular diseases.

Advantageously, the medicament of the present invention is used for treating and/or preventing hypertension, angina such as angina pectoris, Raynaud's disease, arteriopathy, tachycardia, vasospasm, ischemia, myocardial infarction, congestive heart failure, arrhythmia or cerebrovacular accident.

The medicament of the present invention advantageously contains pharmacologically acceptable carriers or excipients.

According to another advantageous embodiment, the medicament of the present invention is intended for oral, topical, or parenteral administration, in particular for intravenous administration.

The medicament of the present invention can be administered in the form of tablets, capsules, solutions, liquids, . . .

According to another advantageous embodiment, the medicament of the present invention is intended for a usage dose of from a few mg/kg to a few g/kg, advantageously from 50 mg/kg to 2000 mg/kg.

The following figures and examples describe and illustrate the present invention but do not restrict the present invention.

FIG. 1 represents the hemodynamic parameters measured in the rat after administration of extracellular hemoglobin obtained from *Arenicola marina* (HbAm).

Figure 1B:
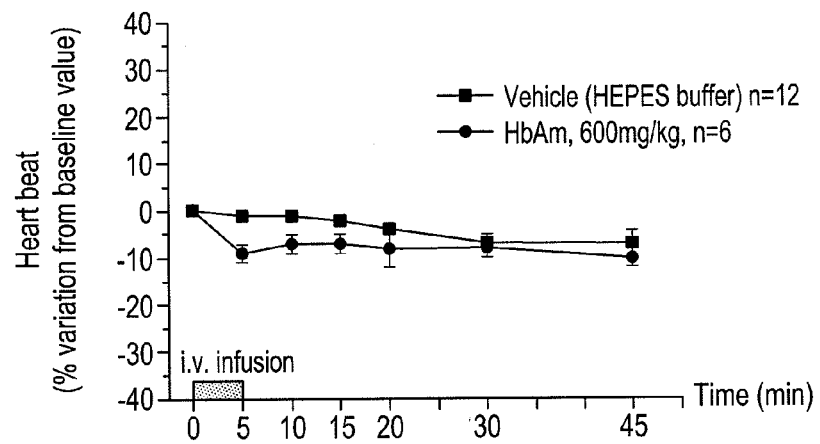
Figure 1C:
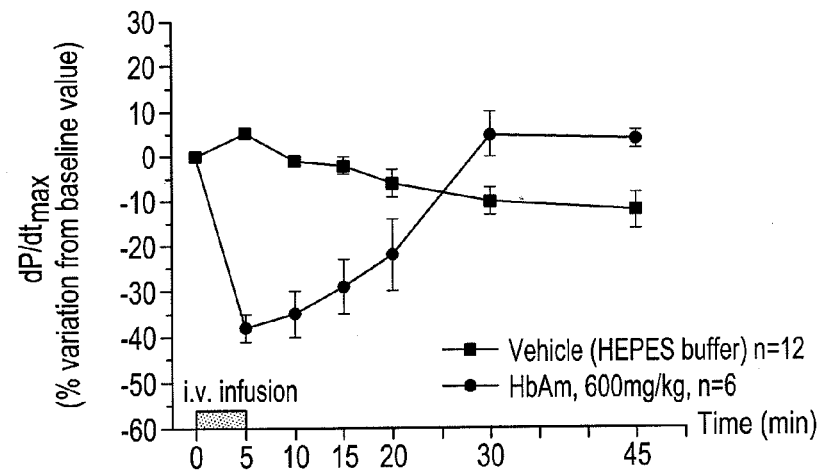

FIG. 1a—Mean Arterial pressure,

FIG. 1b—Heart rate,

FIG. 1c—Myocardial contractility index.

The average results (±standard deviation) obtained for the rats treated with *A. marina* buffer and for the rats treated with HbAm are shown on those FIGS. 1a, b, and c.

FIG. 2 represents the hemodynamic parameters measured in the rat after administration of increasing doses of extracellular hemoglobin obtained from *Arenicola marina* (HbAm).

Figure 2A:
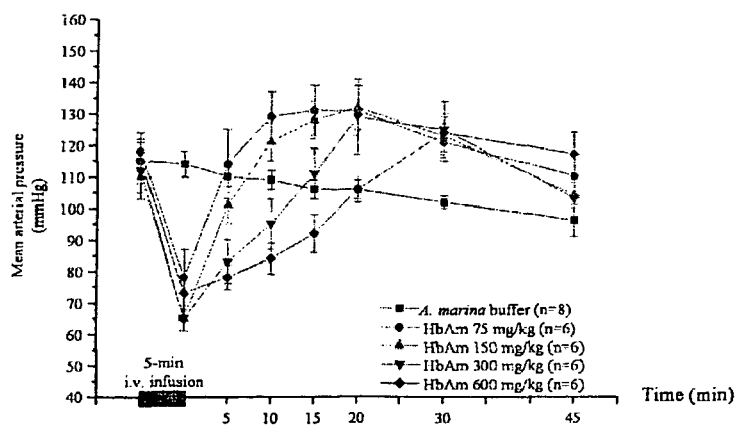
Figure 2B:
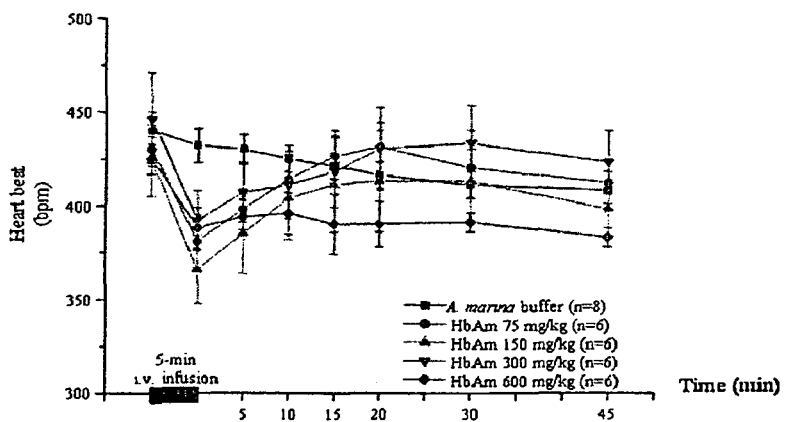
Figure 2C:
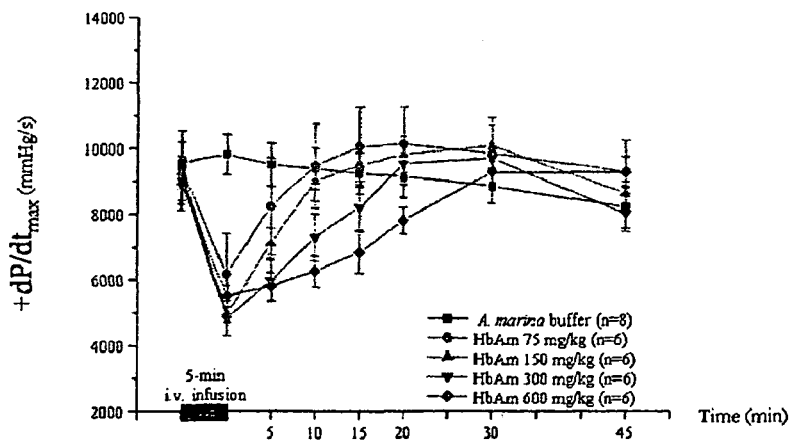

FIG. 2a—Mean Arterial pressure,
FIG. 2b—Heart rate,
FIG. 2c—Myocardial contractility index.

The average results (±standard deviation) obtained for the rats treated with *A. marina* buffer and for the rats treated with HbAm 75, 150, 300, and 600, are shown on those FIGS. 2a, b, and c.

Figure 3:
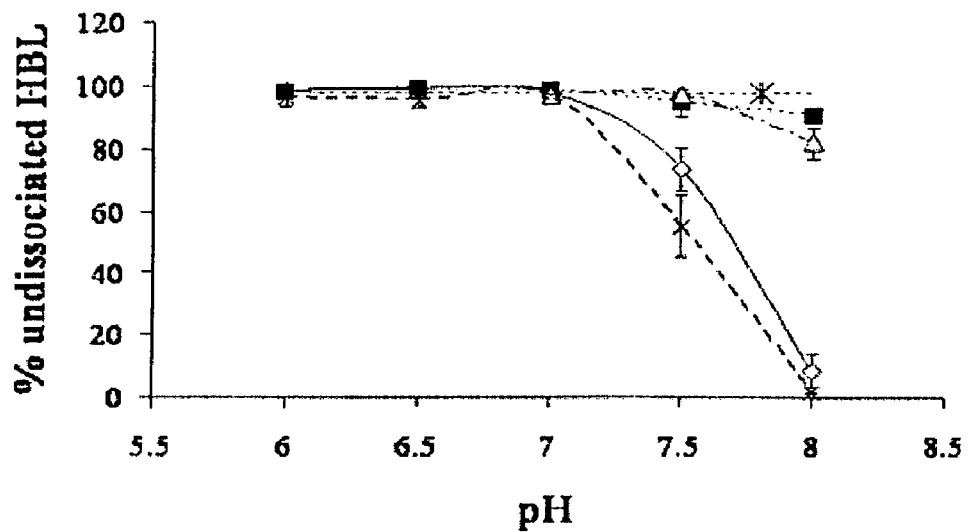

FIG. 3 represents the stabilization of the quaternary structure of HbAm in the presence of divalent ions.

The graph represents the percentage of non-dissociated HbAm just after dilution in buffer, over a pH range from 6.0 to 8.0. This percentage was determined by integrating with the Millennium software the chromatograms obtained by gel filtration at 414 nm, and is represented as a function of pH. Diamonds (◇) represent the dissociation of HbAm in a 0.1 M Tris-HCl buffer, crosses (X) in 0.1 M Tris-HCl+5 mM EDTA, triangles (Δ) in 0.1 M Tris-HCl+50 mM $Mg^{2+}$, squares (■) in 0.1 M Tris-HCl+50 mM $Ca^{2+}$, and asterisks (*) in sea water (pH 7.8). The results are the average ±SD for 3 individual experiments at each point.

Figure 4:
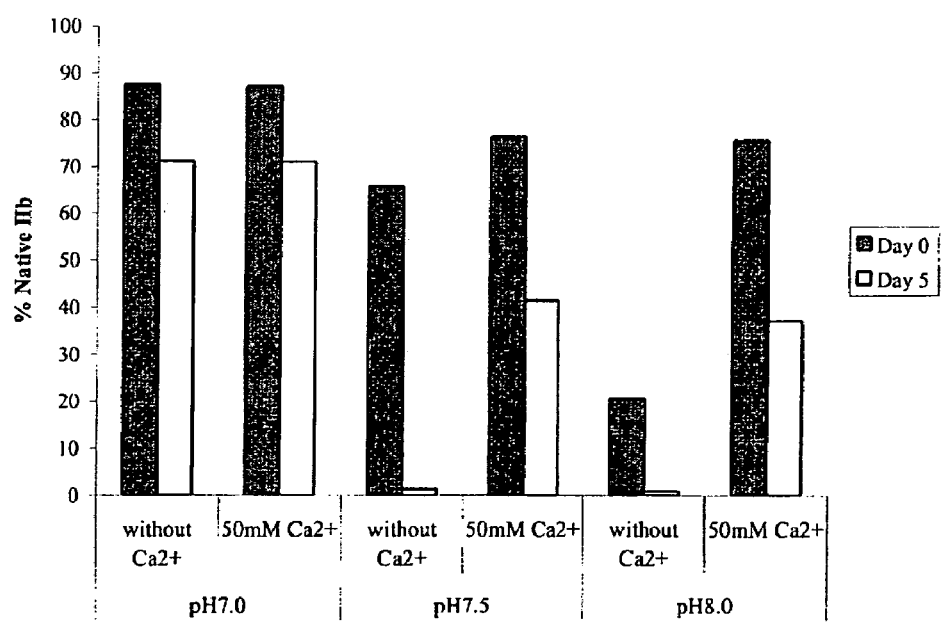

FIG. 4 represents the influence of calcium on the dissociation of HbAm at slightly basic pH over 5 days.

The percentage of non-dissociated HbAm at time zero and at the end of five days is represented at 3 pH levels (7.0, 7.5 and 8.0) in the presence or absence of 50 mM $Ca^{2+}$. At pH 7.0, the HbAm dissociation profile is the same with or without calcium. On the other hand, at pH 7.5 and pH 8.0, the dissociation kinetics slow in the presence of calcium.

Figure 5:
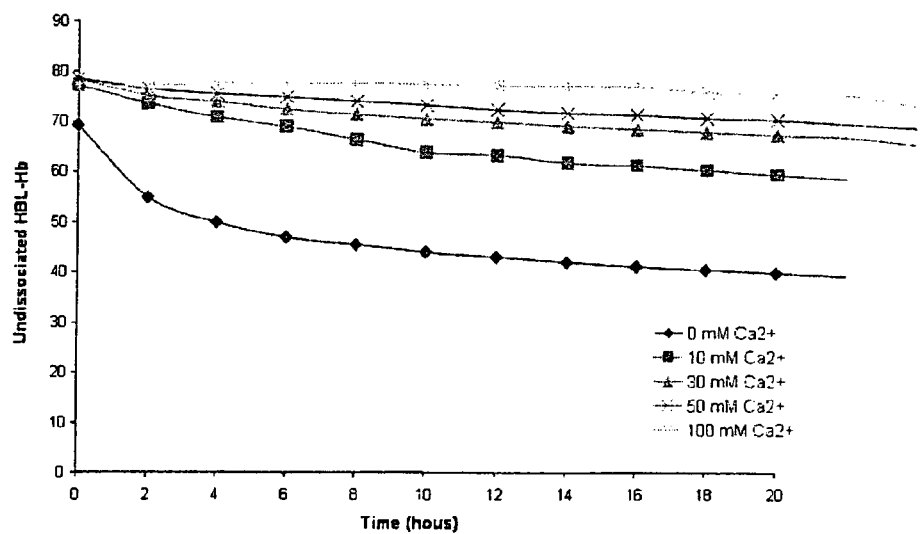

FIG. 5 represents the HbAm dissociation kinetics at pH 7.35 at various concentrations of calcium.

The greater the $Ca^{2+}$ concentration, the slower the dissociation kinetics.

Figure 6:
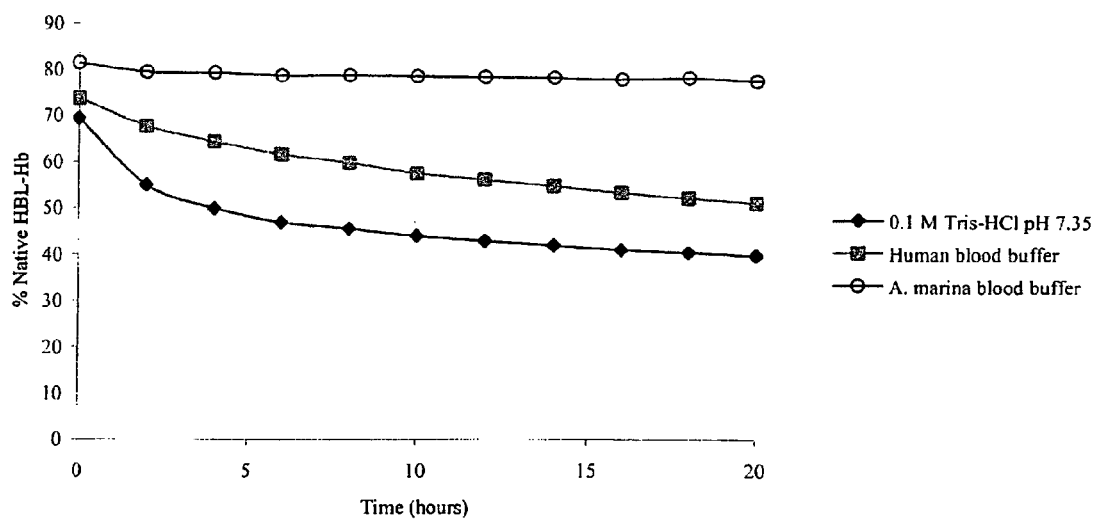

FIG. 6 represents the HbAm dissociation kinetics under three conditions over 20 hours.

The process of dissociation of HbAm is more significant at pH 7.35 in the absence of salts (♦). This process is observed little in the buffer similar to *A. marina* blood composition (○). A relatively significant dissociation process is observed in the buffer of composition similar to human blood (■).

FIG. 7 represents the hemodynamic parameters measured in the rat after co-administration of HbAm and of increasing doses of $CaCl_2$.

Figure 7A:
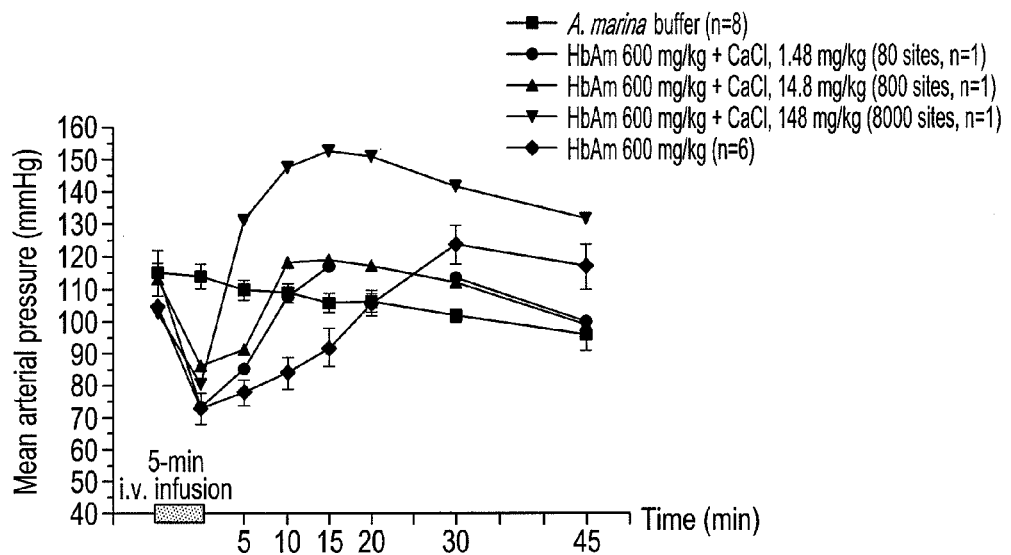
Figure 7B:
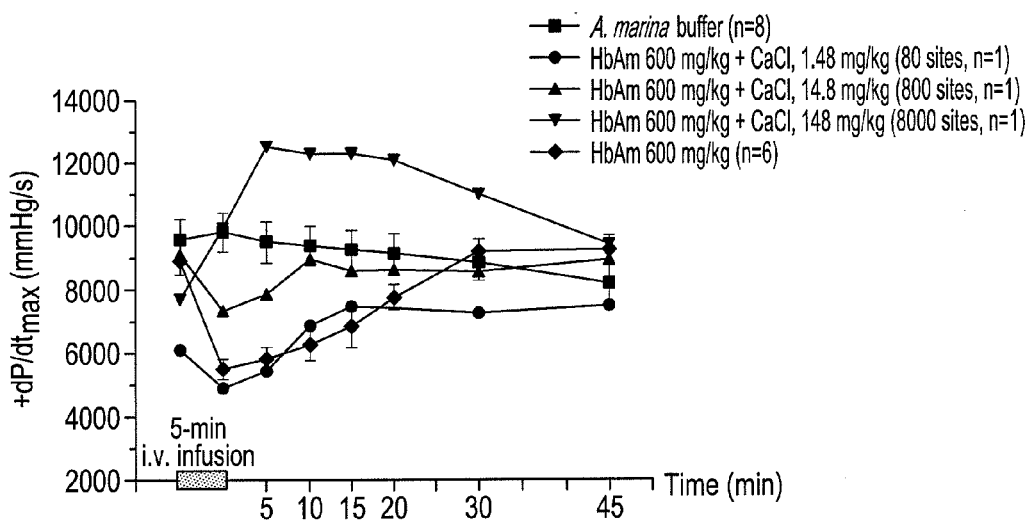

FIG. 7a—Mean Arterial pressure,
FIG. 7b—Myocardial contractility index.

Measurements were performed on a single rat in each case.

FIG. 8 represents the hemodynamic parameters measured in the rat after administration of $Ca^{2+}$-blocked HbAm.

Figure 8A:
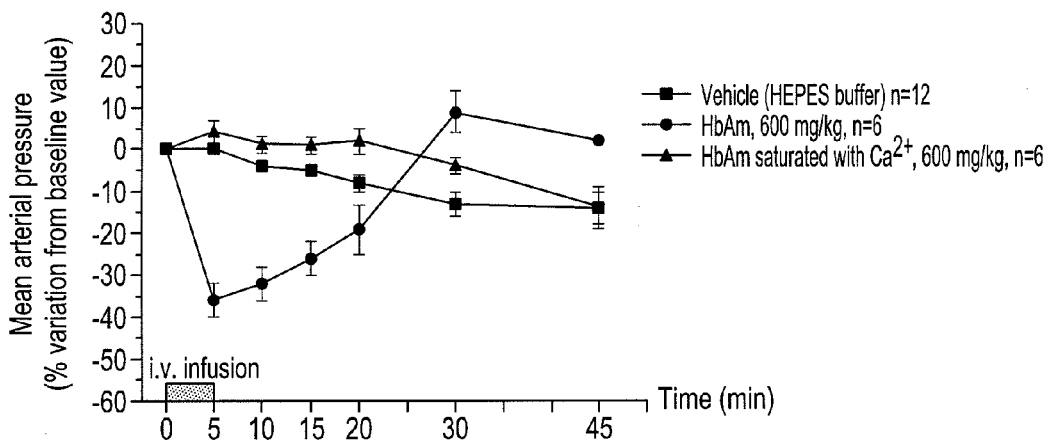
Figure 8B:
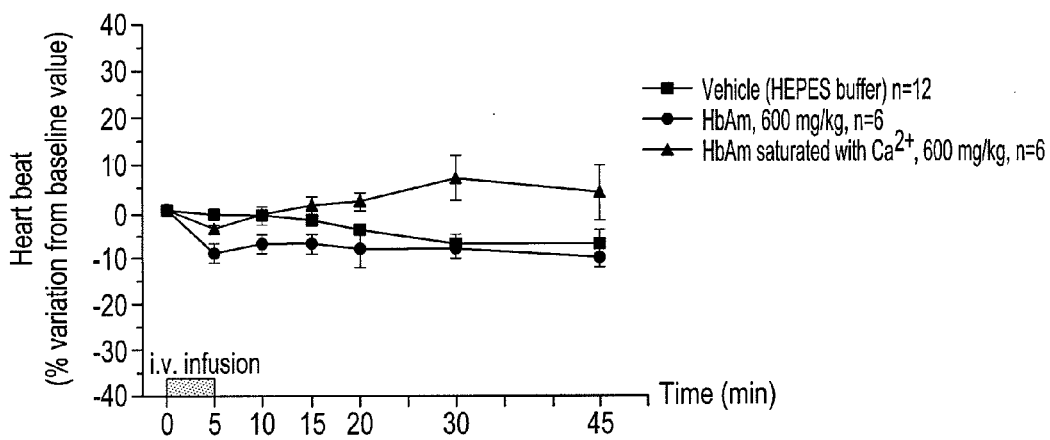
Figure 8C:
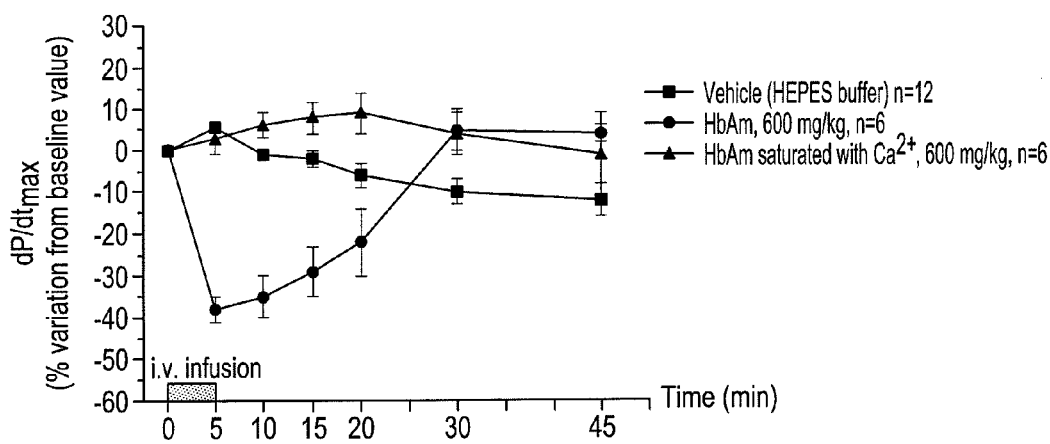

FIG. 8a—Mean Arterial pressure,
FIG. 8b—Heart rate,
FIG. 8c—Myocardial contractility index.

The average results (±standard deviation) obtained for the rats treated with the *A. marina* buffer, for the rats treated with HbAm, and for the rats treated with $Ca^{2+}$-blocked HbAm, are shown on those FIGS. 8a, b, and c.

EXAMPLES

Taking Hemoglobin Samples

The *Arenicola* were harvested at low tide on the foreshore close to Saint-Pol de Leon, North Finistere, France. The blood is taken from the ventral vessel after dissection on a bed of ice. The samples are taken using 1 ml hypodermic syringes equipped with a 25 G×⅝" needle. The samples are collected on ice. After cold centrifugation (15,000 g for 15 min at 4° C.) to eliminate any tissue debris, the supernatants are frozen at −20° C. or in liquid nitrogen, or immediately purified.

Purification of the Hemoglobins

Supernatants are purified by steric exclusion liquid chromatography using a 3×100 cm Sephacryl S-400 column (Amersham Pharmacia Biotech, separation range between 20 and 8,000 kDa). The samples are eluted with *A. marina* saline buffer. The composition of this modified buffer is as follows, for one liter: 8.47 g NaCl (145 mM); 0.29 g KCl (4 mM); 0.04 g $MgCl_2$, $6H_2O$ (0.2 mM) and HEPES (10 mM). The pH is adjusted to pH=6.8 by adding NaOH.

The rate used is generally 0.4 to 0.5 ml/min. The fractions containing the heme are concentrated using Amicon-100 (15 ml) tubes or using an agitation cell retaining the molecules with a weight above or equal to 500,000 Da. Two purification processes following the same protocol could be necessary to obtain pure fractions.

The effect of the administration of extracellular hemoglobin from the annelid polychaete *Arenicola marina* (HbAm) on hemodynamic parameters was evaluated. These experiments made it possible to evaluate the risks of vasoconstriction indirectly.

Example 1

Hypotensive Effect of the Hemoglobin 1.1. Materials and Methods

Experiments were conducted in male Wistar rats (breeding center, Janvier, France) weighing 250-300 g (7 weeks of age). The rats were anesthetized with pentobarbital (60 mg/kg i.p.). A catheter was introduced into a carotid artery in order to measure blood pressure and heart rate. A Millar pressure sensor was introduced into the left ventricular cavity (via the opposite carotid artery) in order to measure left ventricular pressure (LVP). Lastly, a catheter was introduced into the pudendal vein for the intravenous administration of substances. The body temperature of the animals was maintained at approximately 37° C. by using a heating blanket.

1.2. Protocol

After a period of stabilization of the hemodynamic parameters, the extracellular hemoglobin from *Arenicola marina* (HbAm) or *Arenicola marina* buffer (control) solution was administered in a 5-minute intravenous perfusion (administration volume: 1.2 ml/kg/min) and the hemodynamic parameters were followed for 45 min post-administration. Twelve rats were administered the control and 6 the HbAm in a dose of 600 mg/kg. The composition of the *A. marina* buffer is: 145 mM NaCl, 4 mM KCl, 0.2 mM $MgCl_2$, 10 mM Hepes adjusted at pH 6.8 with 2N sodium hydroxide.

The measured parameters were:
Mean Arterial pressure (MAP, mmHg),
Heart rate (HR, beats per min), deived from the blood pressure phase signal,
The maximum peak of the LVP first derivative, dP/dtmax (mmHg/s), an index of myocardial contractility.

1.3. Results

The MAP, HR and myocardial contractility measurements for the control rats and the rats administered HbAm are represented in FIGS. 1a, b, and c for an hemoglobin dose of 600 mg/kg.

The animals treated with *A. marina* buffer (control) presented relatively stable hemodynamic parameters throughout the experiment. The administration of the solution of HbAm in a dose of 600 mg/kg i.v. led to a significant decrease in average blood pressure and in cardiac contractility (FIG. 1). The maximum effect was observed at the end of the perfusion ($T_{5\ min}$) and was −36±4% and −38±3%, respectively (starting from base values, before the administration, of 115±7 mmHg and 8932±501 mmHg/s, respectively). The MAP and dP/dt-max values then returned gradually to the base values, which they reached approximately 30 min after the perfusion began. The heart rate was not changed.

The dose-response effect by administering four different concentrations of HbAm (75, 150, 300 and 600 mg/kg) was then tested. The results are presented in FIGS. 2a, b, and c.

The peak of the effect (reduction in MAP and in cardiac contractility) was little changed as a function of the dose administered. However, the dose effect was observed on the level of the kinetics of the return to the baseline. The higher the dose of HbAm administered, the longer the return to the base value. At a dose of 75 mg/kg, the hypotensive effect observed was highly transitory seeing that it normalized 5 to 10 min after the end of the perfusion. The contractility results followed the same direction.

1.4. Conclusions

The hypotensive effect (reduction in blood pressure) and the negative inotropic effect (reduction in cardiac contractility) observed during the perfusion of a native HbAm solution are dose dependant. This effect is probably due to the binding of $Ca^{2+}$ ions ("fuel" for the contraction of vesicular smooth muscle cells and of myocardial cells) by the HbAm molecule.

It can thus be concluded that HbAm can be efficiently used for therapeutic applications as a hypotensive agent.

The binding of calcium by HbAm was then evaluated.

Example 2

Calcium Binding a) The Stabilizing Effect of Divalent Ions on HbAm Quaternary Structure The studies conducted with respect to properties of HbAm self-assembly revealed the importance of the divalent cations $Ca^{2+}$ and $Mg^{2+}$ in the maintenance of quaternary structure at basic pH. The quaternary structure of HbAm is stabilized at slightly basic pH (7<pH<8) if the salt concentration is similar to that of the sandworm's physiological medium (i.e. isoionic to sea water). Among the salts which allow the maintenance of the quaternary structure, the divalent cations ($Ca^{2+}$ and $Mg^{2+}$) are of utmost importance. These ions prevent dissociation (See FIG. 3) and slow dissociation kinetics (See FIG. 4) of HbAm at alkaline pH. This has been observed for other HBL-hemoglobin annelids, but at pH levels higher than 8.0. However, contrary to *Amphitrite* hemoglobin and *Myxicola* Chl, the divalent ions are not necessary for the maintenance of the structure at neutral and, slightly acid pH, even in the presence of EDTA.

The cations $Ca^{2+}$ and $Mg^{2+}$ stabilize the quaternary structure of HbAm. They can form complexes with 2 side-chain carboxylate groups, $COO^-$-M(II)-$^-OOC$ ionized at alkaline pH, thus stabilizing the structure.

It can thus seen in FIG. 4 that at pH 7.0, the HbAm dissociation profile is the same with or without calcium. On the other hand, at pH 7.5 and pH 8.0, the dissociation kinetics slow in the presence of calcium. The results (FIG. 4) suggest that the stabilization process is instantaneous and substantial at the moment the pH becomes basic, and then it follows dissociation kinetics until all of the calcium present in the solution is bound. Thus, the more the calcium concentration is raised (in vitro conditions) or is replenished (in vivo conditions), the more the stabilization of hemoglobin quaternary-structure will be effective over time. This is demonstrated in FIG. 5 where HbAm is analyzed in the presence of an increasing concentration of calcium at pH 7.35 (physiological pH). The greater the $Ca^{2+}$ concentration, the slower the dissociation kinetics.

II.1. Determination of the Number of Calcium Binding Sites.

II.1.1. Measurement by ICP-MS

The determination of the number of calcium ions per molecule of hemoglobin was carried out according to the protocol detailed by Hagege et al., Assessment of the contribution of inductively coupled plasma mass spectrometry to metalloprotein analysis: a novel approach for studies of multiproteic complexes, *Rapid Commun Mass Spectrum*, 2004, 18, 735-738.

Measurements were taken for 5 batches of purified and de-salted HbAm in a 10 mM ammonium acetate buffer (pH 6.4). The results obtained indicate the number of calcium sites on HbAm at slightly acid pH. By this method, 39.68±0.85 (n=5) $Ca^{2+}$ per hemoglobin were identified, thus approximately 40 potential calcium binding sites at neutral pH.

II.1.2. Colorimetric Assay

A colorimetric assay (Ca-Kit, bioMérieux) was then used to evaluate the number of calcium sites per hemoglobin at basic pH.

pH=7.35; physiological pH

The batches of hemoglobins analyzed were the batches used for the experiments subsequently described. The protocol for the preparation of these hemoglobins is detailed in the following section II.3. 60.15±1.37 (n=7) calcium ions per hemoglobin at pH 7.35 were identified, thus approximately 60 potential calcium binding sites at physiological pH, which is 20 additional HbAm sites compared to neutral pH.

pH=9

Similar experiments were carried out at pH 9.0. For these, HbAm was diluted beforehand in a 0.1 N Tris-HCl+100 mM $Ca^{2+}$ buffer, pH 9.0, for 15 min at 4° C. The HbAm was then dialyzed overnight in MilliQ H2O at 4° C. The hemoglobin assay (Drabkin assay) and calcium assay were performed on the dialyzed batches. 319.66±19.43 (n=6) calcium ions per hemoglobin were identified at pH 9.0, which is approximately 320 potential calcium binding sites at pH 9.0 and which is 8 times more than the number of sites per HbAm at neutral pH.

II.1.2. Conclusions

These experiments revealed the presence of two types of calcium binding sites: 40 sites saturated at neutral pH and ~320 sites saturated at alkaline pH only. Thus, it is logical to think that once HbAm is transfused into human plasma (pH 7.35), it will tend to dissociate and to bind, on the carboxylate groups, the calcium present in the plasma to stabilize its quaternary structure. The number of $Ca^{2+}$ binding sites at pH 7.35 was estimated at 60, which is 20 additional sites compared to neutral pH.

II.2. Consequences During the Administration of HbAm

FIG. 6 shows the HbAm dissociation kinetics under three conditions over 20 hours.

HbAm was thus diluted under three different conditions:
A buffer of ionic composition similar to that of human blood (110 mM NaCl, 5 mM $CaCl_2$, 2 mM $MgSO_4$, 5 mM KCl, 0.1 M Tris-HCl at pH 7.35),
A buffer of ionic composition similar to that of *A. marina* blood (400 mM NaCl, 11 mM $CaCl_2$, 32 mM $MgSO_4$, 3 mM KCl and 0.1 M Tris-HCl at pH 7.4),
A 0.1 M Tris-HCl buffer at pH 7.35.

FIG. 6 confirms the results obtained in FIG. 5: the dissociation kinetics are slowed all the more at alkaline pH since the calcium concentration is high. Indeed, HbAm dissociates more quickly and to a greater degree in the buffer analogous to human blood than in the buffer analogous to *A. marina* blood.

The results obtained in vitro confirm the following hypothesis: HbAm, once administered under human physiological conditions, binds the calcium present in blood to maintain its quaternary structure. This instantaneous reaction would lead to a reduction in the level of physiological calcium and, as a consequence, a reduction in MAP and in the myocardial contractility index observed.

The in vitro results follow the direction of the dose-response effect observed in vivo. The HbAm dissociation kinetics can be schematized in two stages:

A spontaneous dissociation as of the dilution of HbAm at alkaline pH with a substantial binding of physiological calcium. This would cause a major reduction in MAP in vivo.

The dissociation kinetics are then slower and thus the quantity of physiological calcium bound by HbAm is lower. The replenishment of physiological calcium thus has time to reach its base level. However, the higher the concentration of HbAm the longer the return to "normality."

The hypothesis of the calcium inhibitor in vivo by blocking the access to HbAm calcium binding sites was then verified.

b) Blocking HbAm Calcium Binding Sites

After observing the effect of $Ca^{2+}$ on the maintenance of HbAm quaternary structure in vitro, and the hypotensive effect in anesthetized rats, the effects of HbAm saturated with calcium on the cardiovascular rhythm of anesthetized rats were evaluated.

II.3. Calcium Binding-Site Saturation Protocol

In order to block the access of the calcium to the hemoglobin, a protocol was developed to saturate the molecule with calcium before its administration.

Pre-purified batches of HbAm were diluted in a 0.1 M Tris-HCl+00 mM $Ca^{2+}$ buffer, pH 8.0, for 15 min. In this way, dissociation in the presence of excess calcium was induced. The carboxylate groups ionize and bind calcium to maintain the quaternary structure. Next, the HbAm was washed in *A. marina* buffer at pH 7.35 by ultrafiltration on an Amicon-100 kDa at 4° C. The pH of the *A. marina* buffer was adjusted to physiological pH knowing that no dissociation should be observed since the HbAm was saturated with calcium, which ensures its structural integrity. The batch was then analyzed by steric exclusion chromatography. If the quantity of dodecamer (resulting from dissociation) was greater than 3% then the batch was purified by steric exclusion chromatography on a Sephacryl S-400 column to eliminate possible dissociation products. Purification took place in an *A. marina* buffer at pH 7.35. No dissociation should be observed during administration for the preclinical tests and thus the quantity of plasma calcium should remain constant. We prepared 2.5 g of "Ca2+-blocked HbAm" under these conditions for the preclinical control tests.

II.4. Preclinical Tests

II.4.1. First Results

Preliminary analyses were performed by co-administering calcium (in $CaCl_2$ form) with the 600 mg/kg HbAm solution, for blocking the $Ca^{2+}$-binding sites in vivo. For this, the quantity of calcium necessary to block 80, 800 and 8000 potential binding sites was evaluated. The rats were administered and followed as described above. The results obtained are represented in FIG. 7.

When 80 sites were blocked, the peak of the effect on MAP was appreciably the same, but pressure returned to its base value 15 min following the end of the perfusion. With 800 sites potentially blocked, the hypertension was less and the return faster (10 min post-administration). With 8000 $Ca^{2+}$, hypotension persisted during the perfusion with 1 effect peak at the end of the perfusion and then it developed a significant hyperactive phase (probably related to excess Ca).

II.4.2. Results with HbAm Pre-saturated with Calcium

The experiments were carried out under the same conditions as those described previously with "Ca2+-blocked HbAm." The results are represented in FIG. 8.

The administration of a solution of HbAm whose $Ca^{2+}$ binding sites were blocked beforehand does not lead to any reduction in MAP or dP/dtmax. The progression of the hemodynamic parameters in this group is similar to that observed in the control group. Pre-blocking the calcium binding sites on the molecule leads to the complete disappearance of hypotension and of the toxicity observed after the administration of HbAm.

General Conclusions

On the one hand, it was demonstrated that the administration of HbAm did not provoke vasoconstriction problems on the hemodynamic level. However, the administration of HbAm led to instantaneous hypotension followed by a return to normal in the half hour following administration (for a dose of 600 mg/kg). It can thus be concluded that HbAm can be used as a hypotensive agent.

On the other hand, it was revealed that this hypotension was certainly provoked by the significant binding of blood calcium during the administration of HbAm.

Intracellular and extracellular calcium is involved in several phenomena within the organism. Variations in the concentration of intracellular $Ca^{2+}$ play a part in the initiation of electrical and mechanical phenomena: its increase is at the origin of muscular contraction and its reduction is at the origin of relaxation. However, calcium transfer differs according to muscle type, such as cardiac striated muscle, skeletal striated muscle and vascular smooth muscle. Calcium also plays a part in the migration of intracellular organelles, such as receptors and vesicles. It plays a determining role in secretion and in exocytosis phenomena [Dias et al., 2004 Planta med 70: 328-33; Stockes, 2004, J. Clin Hypertens (Greenwich), 6: 192-7; Jewell (2004) J neurosurg 100: 295-302; Fogari (2004) Drug Aging 21: 377-93].

In addition, calcium is essential to cell functioning and replication but its excess has harmful effects. Thus, during oxidative stress or following glutamate receptor hyperstimulation, the increase of intracellular $Ca^{2+}$ leads to the hypercontraction of striated and smooth muscle and the hyperactivation of enzymes, such as the phospholipases and above all the endonucleases, which by modifying DNA take part in apoptosis.

Therefore, it can be concluded that HbAm is able to scavenge excess blood calcium which could lead to various harmful effects such as hypertension, and is thus able to prevent these effects.

The invention claimed is:

1. A method for treating hypertension in a patient, comprising administering to said patient an effective amount of a high molecular weight extracellular hemoglobin having a molecular weight of between 0.1 and 10 million Daltons.

2. The method as claimed in claim 1, wherein the extracellular hemoglobin has a molecular weight of between 1 and 5 million Daltons.

3. The method as claimed in claim 2, wherein the extracellular hemoglobin has a molecular weight of between 3 and 4 million Daltons.

4. The method as claimed in claim 1, wherein the extracellular hemoglobin is naturally polymerized, non-toxic, non-allergenic, and non-immunogenic.

5. The method as claimed in claim 1, wherein the extracellular hemoglobin is obtained from Annelids.

6. The method as claimed in claim 5, wherein the extracellular hemoglobin is obtained from Arenicola marina.

7. The method as claimed in claim 1, wherein the high molecular weight extracellular hemoglobin is administered orally, topically or parenterally.

8. The method as claimed in claim 7, wherein the high molecular weight extracellular hemoglobin is administered intravenously.

9. The method as claimed in claim 1, wherein the high molecular weight extracellular hemoglobin is administered in a dosage range of from 50 mg/kg to 2000 mg/kg.

* * * * *